United States Patent [19]

Okado

[11] Patent Number: 5,348,014

[45] Date of Patent: Sep. 20, 1994

[54] ULTRASONIC DIAGNOSTIC APPARATUS

[75] Inventor: Takeshi Okado, Tochigi, Japan

[73] Assignee: Kabushiki Kaisha Toshiba, Kawasaki, Japan

[21] Appl. No.: 111,899

[22] Filed: Aug. 26, 1993

[30] Foreign Application Priority Data

Aug. 27, 1992 [JP] Japan .................................. 4-228463

[51] Int. Cl.⁵ .............................................. A61B 8/00
[52] U.S. Cl. ............................ 128/660.09; 128/660.01
[58] Field of Search ...................... 128/660.01, 660.08, 128/660.09, 660.10, 662.03

[56] References Cited

U.S. PATENT DOCUMENTS

| 4,362,058 | 12/1982 | Abele | 128/660.09 |
| 4,399,822 | 8/1983 | Theumer | 128/660.09 |
| 5,167,165 | 12/1992 | Brucher et al. | 128/660.09 |
| 5,170,790 | 12/1992 | Lacoste et al. | 128/660.09 |

FOREIGN PATENT DOCUMENTS 62-59007  4/1987  Japan .
1-124441  5/1989  Japan .

Primary Examiner—George Manuel
Attorney, Agent, or Firm—Oblon, Spivak, McClelland, Maier & Neustadt

[57] ABSTRACT

An ultrasonic diagnostic apparatus comprising an ultrasonic diagnostic apparatus main body, a cable, one end of which is attached to the ultrasonic diagnostic apparatus main body, an ultrasonic probe attached to the other end of the cable, an arm unit including a plurality of arm members which rotate and slide with respect to one another, and a balancer unit. The balancer unit is attached to an end of the arm unit and substantially balances the weight of the ultrasonic probe. The balancer unit comprises a rotational mechanism using a constant force spring for generating a constant winding force smaller than the weight of the ultrasonic probe, irrespective of the length of the a handing unit of the cable, and a wire for providing the winding force.

12 Claims, 3 Drawing Sheets

ULTRASONIC DIAGNOSTIC APPARATUS

BACKGROUND OF THE INVENTION

1. Field of the Invention

The present invention relates to an ultrasonic diagnostic apparatus having an arm mechanism for supporting an ultrasonic probe.

2. Description of the Related Art

A conventional ultrasonic diagnostic apparatus will be described with reference to FIG. 1. As shown in FIG. 1, an ultrasonic diagnostic apparatus 10 comprises an ultrasonic diagnostic apparatus main body 20, an ultrasonic probe 30 and an arm mechanism 40.

The ultrasonic probe 30 has an ultrasonic probe body 31, a cable 32, and a probe side connector 33 which is detachably attached to a body side connector 24 provided in the ultrasonic diagnostic apparatus main body 20.

The arm mechanism 40 is constituted by an arm unit 41 and a cable guide unit 42. The arm unit 41 includes an arm body 41A and an attachment member 41B. One end of the arm body 41A is fixed to the ultrasonic diagnostic apparatus main body 20 by the attachment member 41B. The cable guide unit 42 is attached to the other end of the arm body 41A. The cable 32 of the ultrasonic probe 30 is hung up and guided by the cable guide unit 42.

When a subject 200 is diagnosed with the ultrasonic diagnostic apparatus 100, an operator (not shown) holds the probe body 31 of the ultrasonic probe 30 by hand and applies an ultrasound transmitting and receiving surface of the probe body 31 to the subject 200.

with the above-mentioned arm mechanism 40, since the cable 32 is guided by the cable guide unit 42, the probe body 31 can be moved smoothly in the air or on the surface of the body of the subject 200.

In recent years, a large-size ultrasonic probe of mechanical scanning type, which is several times heavier than the probe body 31 of the normal electronic scanning type, has been developed. If the ultrasonic probe of the mechanical type is hung, using the conventional arm mechanism 40, the following problem may arise: when the operator holds the ultrasonic probe for a long period of time for a routine inspection, he or she suffers from wrist-strain; when the operator palpates the subject during scanning, it is difficult to hold the heavy ultrasonic probe, resulting in low operability; and since the ultrasonic probe presses on the body of the subject 200, it not only inflicts pain on the subject but also makes it difficult to obtain an accurate image, which adversely affects the diagnosis.

SUMMARY OF THE INVENTION

It is accordingly an object of the present invention to provide an ultrasonic diagnostic apparatus which can be handled easily and achieve reliable diagnosis.

The above object can be achieved by an ultrasonic diagnostic apparatus comprising:

an ultrasonic diagnostic apparatus main body;

a cable, one end of which is attached to the ultrasonic diagnostic apparatus main body;

an ultrasonic probe attached to the other end of the cable; and an arm mechanism having an arm unit and a balancer unit which is provided at one end of the arm unit, substantially balance the weight of the ultrasonic probe.

The above object can also be achieved by an ultrasonic diagnostic apparatus comprising:

an ultrasonic diagnostic apparatus main body;

a cable, one end of which is attached to the ultrasonic diagnostic apparatus main body;

an ultrasonic probe attached to the other end of the cable;

an attachment member fixed to the ultrasonic diagnostic apparatus;

an extendible support, one end of which is fixed to the attachment member;

a hinge, one end of which is fixed to the other end of the extendible support;

an extendible arm, one end of which is fixed to the other end of the hinge;

a balancer, provided at the other end of the extendible arm, to substantially balance the weight of the ultrasonic probe, the balancer having a rotation mechanism using a constant force spring for generating a constant winding force, which is smaller than the weight of the ultrasonic probe, irrespective of the length of a hanging unit of the cable, and a wire for providing the winding force; and a probe holding member, connected to an end of the wire of the balancer, for holding the ultrasonic probe.

According to the present invention, since the ultrasonic probe is held while the balance of the probe is being kept or substantially kept, the operator can hold the probe with a reduced weight. It is, thus, possible for the operator to hold the ultrasonic probe with ease for a long period of time. In addition, since the ultrasonic probe can be suspended at a desired height, it can be left in the air, or stay at a substantially balanced position when it is not being used. Further, since the ultrasonic probe assumes a reduced weight, the pressure on the surface of the subject is reduced, resulting in the operability of the apparatus and the reliability of the diagnosis being improved.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

DETAILED DESCRIPTION OF THE PREFERRED EMBODIMENT

Figure 1:
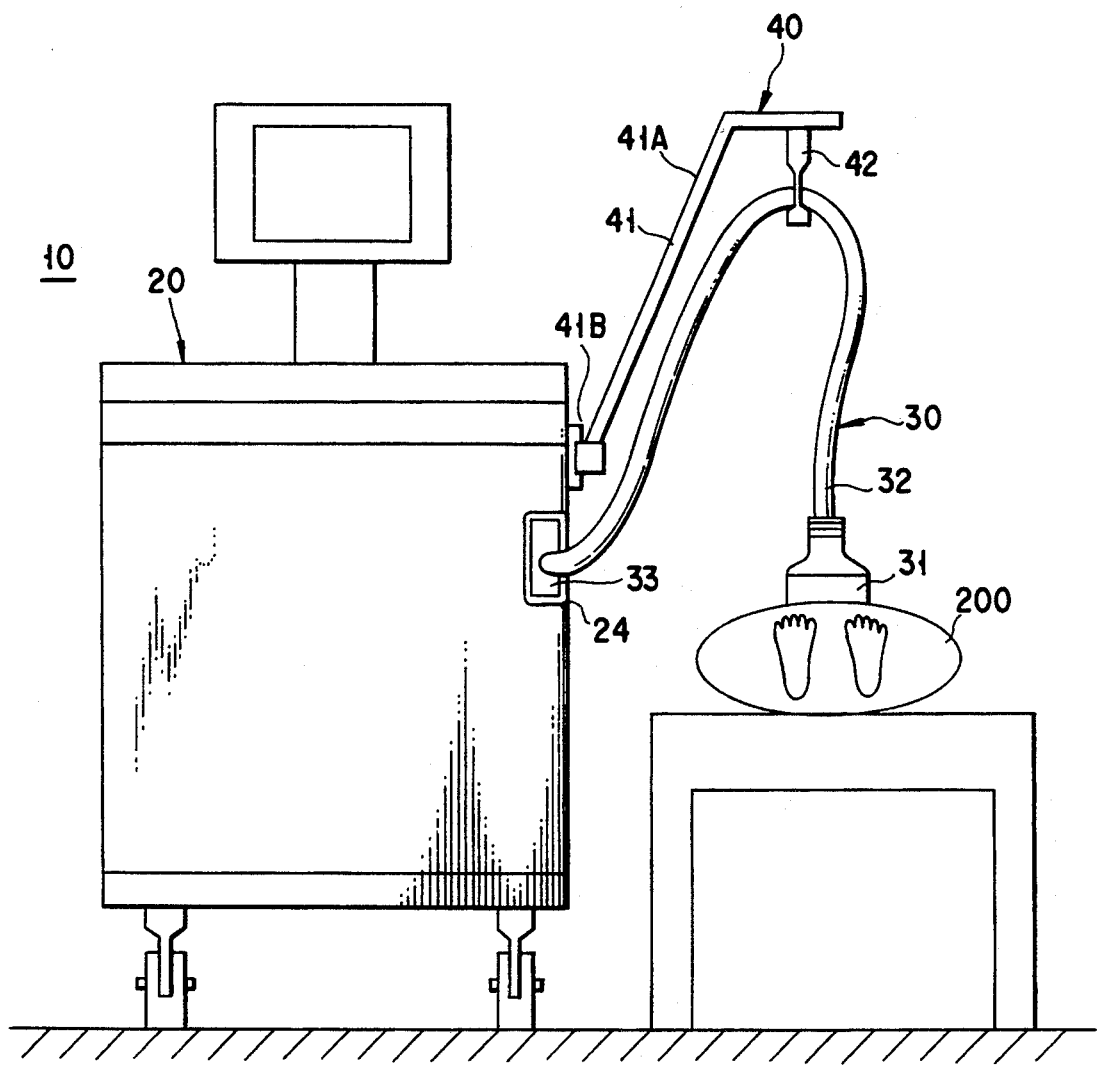
FIG. 1 is a diagram showing a conventional ultrasonic diagnostic apparatus.
Figure 2:
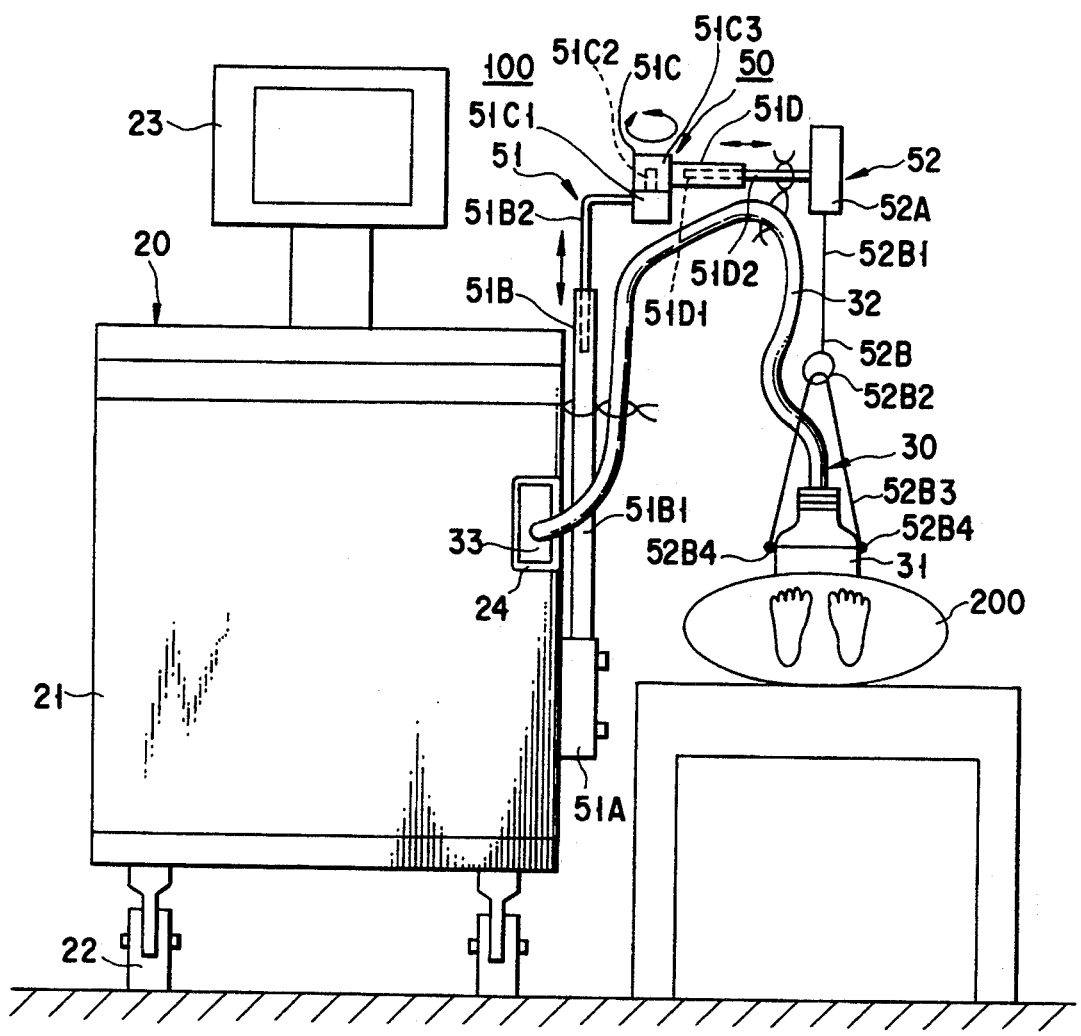
FIG. 2 is a diagram showing an ultrasonic diagnostic apparatus according to an embodiment of the present invention.

An arm mechanism for use in an ultrasonic diagnostic apparatus according to an embodiment of the present invention will be described with reference to FIG. 2. As shown in FIG. 2, an ultrasonic diagnostic apparatus 100 of the embodiment comprises an ultrasonic diagnostic apparatus main body 20, an ultrasonic probe 30 and an arm mechanism 50.

The ultrasonic diagnostic apparatus main body 20 comprises a casing 21, casters 22 provided under the casing 21, and a monitor 23 mounted on the casing 21. The casing 21 includes an operation unit and a signal processing unit. A casing side connector 24 is provided on a side wall of the casing 21.

The ultrasonic probe 30 comprises a probe body 31, a cable 32, and a probe side connector 33. An electronic scanning probe or mechanical scanning probe is typically used as the probe body 31. Through the cable 32, a transmission signal is transmitted from the main body 20 to the probe body 31, a reception signal is transmitted from the probe body 31 to the main body 20, and a control signal is transmitted between the main body 20 and the probe body 31. The probe side connector 33 is connected to the proximal end unit of the cable 32, and detachably connected to the casing side connector 24.

The arm mechanism 50 consists of an arm unit 51 and a balancer unit 52. It holds the ultrasonic probe 30 at a desired position while a weight W of the probe 30 is balanced or substantially balanced. More specifically, the balancer unit 52 holds the probe body 31 in a balanced or substantially state at a desired height with winding force $T_0$, which is substantially equal to the weight W of the probe body 31.

The arm unit 51 consists of an attachment member 51A, an extendible support 51B, a hinge 51C, and an extendible arm 51D to which the balancer unit 52 is attached.

The attachment member 51A is fixed to the casing 21 of the ultrasonic diagnostic apparatus main body 20.

The extendible support 51B consists of a fixed pipe 51B1 and a movable L-shaped pipe 51B2. One end of the fixture pipe 51B1 is fixed to the attachment member 51A. One end of the movable L-shaped pipe 51B2 is inserted through the other end of the fixed pipe 51B1 with a predetermined frictional force. A fixed piece 51C1 of the hinge 51C is fixed to the other end of the movable L-shaped pipe 51B1. The degree of extension of the extendible support 51B is adjusted by changing the length of the unit of the movable L-shaped pipe 51B2 which is inserted through the fixed pipe 51B1. Adjustment of extension of the extendible support 51B corresponds to adjustment of the height of the balancer unit 52 and the probe body 31.

The hinge 51C of the arm unit 51 consists of the above-mentioned fixed piece 51C1 which is fixed to the other end of the movable L-shaped pipe 51B2, a vertical shaft 51C2 provided in the fixed piece 51C1, and a movable piece 51C3 which is rotatable about the vertical shaft 51C2 and to which the extendible arm 51D is fixed. Adjustment of rotation of the movable piece 51C3 with respect to the fixed piece 51C1 corresponds to adjustment of a horizontal position of the balancer 52 and the probe body 31.

The extendible arm 51D of the arm unit 51 consists of a fixed pipe 51D1, one end of which is fixed to the movable piece 51C3 of the hinge 51C, and a movable pipe 51D2, one end of which is inserted to the other end of the fixed pipe 51D1. The degree of extension of the extendible arm 51D is adjusted by changing the length of the unit of the movable pipe 51D2 which is inserted through the fixed pipe 51D1. Adjustment of extension of the extendible arm 51D corresponds to adjustment of horizontal positions of the balancer unit 52 and the probe body 31.

The balancer unit 52 consists of a balancer 52A and a probe holding member 52B. A constant force coil spring balancer using a constant force spring is used as the balancer 52A. A constant force coil spring, a type of coil spring, is wound tight when no load is applied, and when the distal end thereof is drawn, it generates a constant recovery force (winding force $T_0$), irrespective of the length of the drawn unit (stroke).

Figure 3:
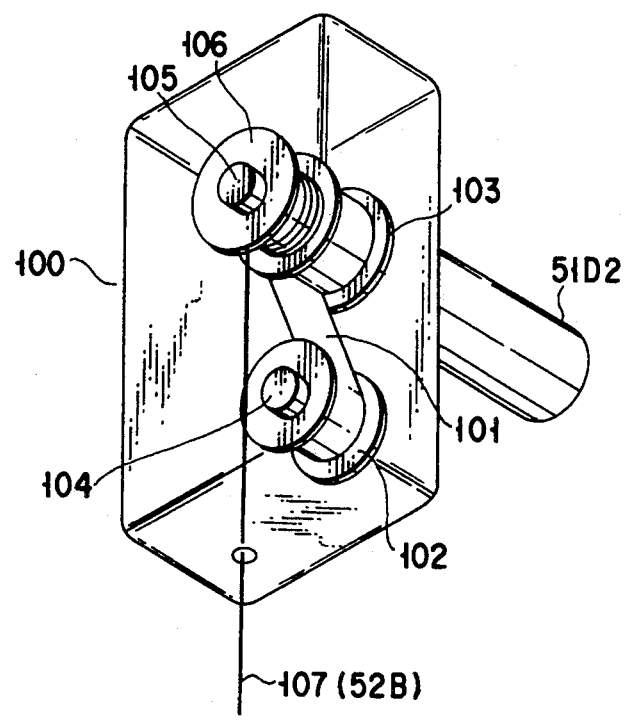
FIG. 3 is a perspective view showing an example of the balancer.

A constant torque rotation mechanism using the constant force coil spring will now be described. As shown in FIG. 3, a casing 100 includes a first drum 102 having a diameter slightly greater than that of the free coil diameter of a constant force spring 101, a second drum 103 having a diameter slightly greater than that of the first drum 102. The first drum 102 has a shaft 104, and the second drum 103 has a shaft 105. The drums 102 and 103 and the shafts 104 and 105 are freely rotatable. A wire drum 106 is directly connected to the shaft 105. The constant force spring 101 is wound around the first drum 102. The outer end of the spring 101 is drawn and fixed to the second drum 103. The second drum 103 is rotated and winds the spring 101 in the reverse direction. In this state, the spring 101 generates a constant force (torque T) in a direction in which the spring is to be recovered to the diameter of the first drum 102 which is slightly greater than the free coil diameter of the spring 101.

As described above, a constant torque rotation mechanism can be achieved by the constant force coil spring. In the constant force coil spring balancer 52A of this embodiment, since the torque T acts also on the wire drum 106 directly attached to the second drum 103, the torque T and the winding force $T_0$ based on the diameter of the wire drum 106 also act on a wire 107 attached to the wire drum 106.

A flat spiral spring balancer using a flat spiral spring can be used as the balancer instead of the constant force coil spring balancer 52A shown in FIG. 3.

The probe holding member 52B consists of a wire 52B1, a ring 52B2, a supporting cord 52B3, and fixture members 52B4. One end of the wire 52B1 is attached to the balancer 52A, and the other end thereof is attached to the ring 52B1. The supporting cord 52B3 is inserted through the ring 52B2. Both ends of the supporting cord 52B3 are fixed to the fixture members 52B4. The fixture members 52B4 are fixed near the center of the gravity of the probe body 31.

The present embodiment is particularly characterized in that the winding force $T_0$ is substantially equal to the weight W of the probe body 31. This makes it possible to hold the ultrasonic probe 30 at a desired position in horizontal and vertical directions, in a state where the weight W of the probe body 31 is balanced.

Referring to the relationship between the winding force $T_0$ and the weight w of the probe body 31, there are two conditions: $T_0 < W$ (condition A); and $T_0 > W$ (condition B). In condition A, if the weight W of the probe body 31 is 300 g, $T_0$ is set to, for example, 200 g.

Figure 4:
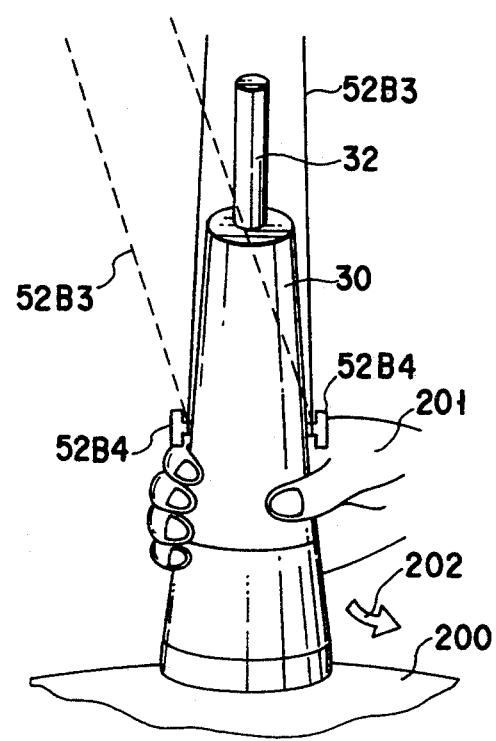
FIG. 4 is a diagram showing a state wherein an ultrasonic probe is applied to the surface of the body of the subject.

If the condition A ($T_0 < W$) is not satisfied, a hand 201 of the operator holds the probe body 31. In FIG. 4, the probe body 31 is brought into contact with the surface of the subject 200 at right angles. If the probe body 31 is inclined in a direction indicated by an arrow 202 so that the supporting cord 52B3 is in a position indicated by the broken line, a moment is generated at the fixing members 52B4 and acts on the hand 201 of the operator.

In contrast, if the condition A ($T_0 < W$) is satisfied, the above-mentioned moment, applied to the probe 31, acts to move it upwards. If the winding force $T_O$ is set such that sum of the load corresponding to the moment and the winding force $T_0$ is substantially equal to the weight W of the probe body 31, the moment does not substantially act on the hand 201 of the operator. Therefore, the operator does not suffer from wrist-strain, resulting in improvement of the operability.

The condition B ($T_0 < W$) is suitable in a case where the moment is a force to move the probe body 31 downwards. This is a case where the distal end of the probe body is directed excessively downwards.

The total length of the wire 52B is set smaller than the distance between the balancer unit 52 and the bottom of the ultrasonic diagnostic apparatus main body 21. Therefore, even when the probe 30 is released from the operator's hand, it does not drop to the floor.

As has been described above, according to the embodiment, the balancer unit 52 holds the probe body 31 in a state where the weight W of the ultrasonic probe 30 (the probe body 31) is balanced. Since the operator thus holds the probe body 31 with a reduced weight, he or she can easily hold the probe for a long period of time during diagnosis. In addition, since the probe body 31 can be suspended at a desired height, when the operator palpates the subject during scanning, the probe body 31 can be left in the air near the palpated unit of the subject. Further, since the probe body 31 assumes a reduced weight, the pressure on the surface of the subject is reduced, resulting in the operability of the apparatus and the reliability of the diagnosis being improved.

Therefore, the present invention can provide an ultrasonic diagnostic apparatus which can be handled easily and achieve reliable diagnosis.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An ultrasonic diagnostic apparatus comprising:
   an ultrasonic diagnostic apparatus main body;
   a cable, one end of which is attached to the ultrasonic diagnostic apparatus main body;
   an ultrasonic probe attached to the other end of the cable;
   an arm unit fixed to the ultrasonic diagnostic apparatus; and
   a balancer unit provided at one end of the arm unit, so as to substantially balance the weight of the ultrasonic probe, the balancer unit comprising a rotational mechanism using a constant force spring for generating a winding force of a constant torque.

2. The ultrasonic diagnostic apparatus according to claim 1, wherein the winding force generated in the balancer unit is smaller than the weight of the ultrasonic probe.

3. The ultrasonic diagnostic apparatus according to claim 1, wherein the winding force generated in the balancer unit is greater than the weight of the ultrasonic probe.

4. The ultrasonic diagnostic apparatus according to claim 1, wherein the arm unit comprises a plurality of arm members which rotate and/or slide with respect to one another.

5. The ultrasonic diagnostic apparatus according to claim 1, wherein the arm unit comprises:
   an attachment member fixed to the ultrasonic diagnostic apparatus;
   an extendible support, one end of which is fixed to the attachment member;
   a hinge, one end of which is fixed to the other end of the extendible support; and
   an extendible arm, one end of which is fixed to the other end of the hinge, and the other end of which is attached to the balancer unit.

6. The ultrasonic diagnostic apparatus according to claim 5, wherein the extendible support comprises:
   a fixed pipe, one end of which is connected to the attachment member; and
   a movable L-shaped pipe, one end of which is inserted to the other end of the fixed pipe, and the other end of which is fixed to the one end of the hinge.

7. The ultrasonic diagnostic apparatus according to claim 5, wherein the hinge comprises:
   a fixed piece which is fixed to the distal end of the extendible support;
   a shaft attached to the fixed piece; and
   a movable piece, to which the one end of the extendible arm is attached and which is rotatable about the shaft.

8. The ultrasonic diagnostic apparatus according to claim 5, wherein the extendible arm comprises:
   a fixed pipe, one end of which is fixed to the other end of the hinge; and
   a movable pipe, one end of which is inserted to the fixed pipe and the other end of which is attached to the balancer unit.

9. The ultrasonic diagnostic apparatus according to claim 1, wherein the balancer unit comprises:
   a balancer including a rotational mechanism using a constant force spring for generating a winding force of a constant torque and a wire for providing the winding force generated by the rotational mechanism; and
   a probe holding member, to which an end of the wire is connected, for holding the ultrasonic probe.

10. The ultrasonic diagnostic apparatus according to claim 9, wherein the balancer comprises:
    a casing;
    a constant force spring having a fixed end and a free end; and
    a drum, which is rotated by a recovery force generated at the free end and on which the wire is wound.

11. The ultrasonic diagnostic apparatus according to claim 9, wherein the total length of the wire is smaller than the distance between the balancer unit and the bottom of the ultrasonic diagnostic apparatus main body.

12. An ultrasonic diagnostic apparatus comprising:
    an ultrasonic diagnostic apparatus main body;
    a cable, one end of which is attached to the ultrasonic diagnostic apparatus main body;

an ultrasonic probe attached to the other end of the cable;

an attachment member fixed to the ultrasonic diagnostic apparatus;

an extendible support, one end of which is fixed to the attachment member;

a hinge, one end of which is fixed to the other end of the extendible support;

an extendible arm, one end of which is fixed to the other end of the hinge;

a balancer, provided at the other end of the extendible arm, to substantially balance the weight of the ultrasonic probe, said balancer having a rotation mechanism using a constant force spring for generating a constant winding force, which is smaller than the weight of the ultrasonic probe, irrespective of the length of a hanging unit of the cable, and a wire for providing the winding force; and a probe holding member, connected to an end of the wire of the balancer, for holding the ultrasonic probe.

* * * * *